United States Patent [19]
Sezginer et al.

[11] Patent Number: 5,705,927
[45] Date of Patent: Jan. 6, 1998

[54] PULSED NUCLEAR MAGNETISM TOOL FOR FORMATION EVALUATION WHILE DRILLING INCLUDING A SHORTENED OR TRUNCATED CPMG SEQUENCE

[75] Inventors: Abdurrahman Sezginer, Brookfield; Douglas D. Griffin, Bethel, both of Conn.

[73] Assignee: Schlumberger Technology Corporation, Ridgefield, Conn.

[21] Appl. No.: 623,031

[22] Filed: Mar. 28, 1996

Related U.S. Application Data

[60] Division of Ser. No. 337,784, Nov. 14, 1994, abandoned, which is a continuation-in-part of Ser. No. 200,815, Feb. 22, 1994, abandoned, which is a continuation of Ser. No. 922,254, Jul. 30, 1992, abandoned.

[51] Int. Cl.$^6$ ............................................. G01V 3/32
[52] U.S. Cl. ............................................. 324/303
[58] Field of Search ............................. 324/303, 306, 324/300, 359, 356

[56] References Cited

U.S. PATENT DOCUMENTS

| | | | |
|---|---|---|---|
| 4,710,713 | 12/1987 | Strikman | 324/303 |
| 4,792,757 | 12/1988 | Vail, III et al. | 324/303 |
| 4,949,045 | 8/1990 | Clark et al. | 324/338 |
| 5,280,243 | 1/1994 | Miller | 324/303 |

*Primary Examiner*—Sandra L. O'Shea
*Assistant Examiner*—Roger Phillips
*Attorney, Agent, or Firm*—Leonard W. Pojunas; Brigitte L. Jeffery; David Garrod

[57] ABSTRACT

The instruments of a pulsed nuclear magnetic resonance (NMR) device are included in a drill collar for evaluating earth formations. The resulting tool makes NMR measurements while the formation is being drilled. Permanent magnets produce a static field in the earth formation. Shimming permanent magnets inside or outside the drill collar suppress the magnetic resonance of borehole fluids. The permanent magnets are manufactured from two magnetic materials, for example.

9 Claims, 9 Drawing Sheets

PULSED NUCLEAR MAGNETISM TOOL FOR FORMATION EVALUATION WHILE DRILLING INCLUDING A SHORTENED OR TRUNCATED CPMG SEQUENCE

This is a divisional of U.S. application Ser. No. 08/337,784 filed Nov. 14, 1994, now abandoned, which is a continuation-in-part of U.S. application Ser. No. 08/200,815, filed Feb. 22, 1994, abandoned, which is a continuation of U.S. application Ser. No. 07/922,254, filed Jul. 30, 1992, abandoned.

FIELD OF THE INVENTION

The invention concerns a tool for logging while drilling. More specifically the invention concerns a tool for logging a formation using pulsed nuclear magnetic resonance (NMR) techniques while drilling a borehole into the formation.

BACKGROUND OF THE INVENTION

Several pulsed NMR tools have been designed for borehole deployment via wireline and are described in U.S. Pat. Nos.:

4,350,955, issued September 1982 to Jackson et al.;

4,629,986, issued December 1986 to Clow et al.;

4,710,713, issued December 1987 to Strikman;

4,717,876, issued January 1988 to Masi et al.;

4,717,877, issued January 1988 to Taicher et al.;

4,717,878, issued January 1988 to Taicher et al.;

4,714,881, issued December 1987 to Givens;

5,023,551, issued June 1991 to Kleinberg et al.;

5,055,787, issued October 1991 to Kleinberg et al.; and 5,055,788, issued October 1991 to Kleinberg et al.

All of these patents describe NMR tools which employ permanent magnets to polarize hydrogen nuclei, and RF coils to excite and detect nuclear magnetic resonance to determine porosity, free fluid ration, or permeability of a formation, for example. The tools described in U.S. Pat. Nos. 4,717,877; 5,055,787; and 5,055,788 have been successfully tested in boreholes.

The instrument concepts described in the related U.S. Pat. Nos. 4,710,713 and 4,717,877 have a rotationally invariant region of resonance, which is a thin cylindrical shell coaxial with the borehole. The electromagnetic fields have a simple azimuthal dependence: both the static and RF fields at any point in the vicinity of the instrument rotate at the same rate as the instrument rotates. The rotation does not disturb the NMR measurement because the nuclear magnetic moment adiabatically tracks the direction of the magnetic field. The radial thickness of the resonance region of these instruments is on the order of 1 mm.

The instrument concepts described in the related U.S. Pat. Nos. 4,350,955, 4,629,986, and 4,717,876 have rotationally invariant static and RF fields and a relatively large resonant region (at least 10–30 mm thick). The resonant region is thicker because the magnitude of the magnetic field is stationary at the resonant region. These patents, however, do not describe rotating the instruments.

Several logging while drilling (LWD) and measuring while drilling (MWD) tools have been designed for formation evaluation while drilling and drill string characterization while drilling, respectively. Logging or measuring instruments are placed in drill collars up to 100 ft behind the drill bit. An MWD tool is described in U.S. Pat. Nos. 3,777,560 to Guinard and 4,479,564 to Tanguy. An LWD tool is described in U.S. Pat. Nos. 4,899,112 to Clark et al. and 4,949,045 to Clark et al. Typically, these tools use electromagnetic techniques in evaluating resistivity of a formation while drilling.

None of the NMR tools have been used in a drilling string, nor have the LWD or MWD tools used pulsed NMR techniques.

SUMMARY OF THE INVENTION

One aspect of the invention concerns an apparatus comprising: a drilling means for drilling a borehole in an earth formation; a measuring means for making nuclear magnetic resonance (NMR) measurements while the borehole is being drilled; and a means for carrying fluid through the drilling means. The measuring means comprises: a) at least one magnet for reducing a resulting magnetic resonance signal of the borehole fluid and for producing a static magnetic field in the formation; and b) a means for producing an oscillating field in the formation.

In one embodiment, the invention concerns a drill string and bit for drilling a borehole in an earth formation and a pulsed NMR device which is housed by the drill string. The embodiment includes a channel within the drill string and pulsed NMR device through which drilling mud is pumped into the borehole. The pulsed NMR device comprises two permanent magnets which are mounted within the drill collar to surround the channel. The pulsed NMR device also includes an antenna coil mounted in a recess in the exterior surface of the drill string and between the two permanent magnets, and a third permanent magnet. The third permanent magnet suppresses magnetic resonance in the borehole fluid. The third permanent magnet can be positioned with the antenna coil in the recess, or with the other two permanent magnets within the drill collar. Also, dual material permanent magnets reduce the cost of an associated NMR tool without affecting operation of the NMR tool.

DETAILED DESCRIPTION

Because the resonance region of the instruments of U.S. Pat. Nos. 4,710,713 and 4,717,877 is one the order of 1 mm, it is expected that lateral vibrations of a drill collar which might be proposed for containing an NMR device would adversely affect an NMR measurement. For example, a lateral, 50 Hz vibration of 1 mm amplitude (100 g acceleration) would disable the measurement. Also, the inventors have determined that, since the drill string can make 0.1 or up to several revolutions in the duration of a pulsed NMR measurement (on the order of 0.01 to 1 second), an NMR instrument in a drilling string must be rotationally symmetric. Accordingly, the instrument of this invention provides greater immunity to lateral motion and is also rotationally symmetric about a longitudinal axis. A detailed description of the tool follows.

Figure 1:
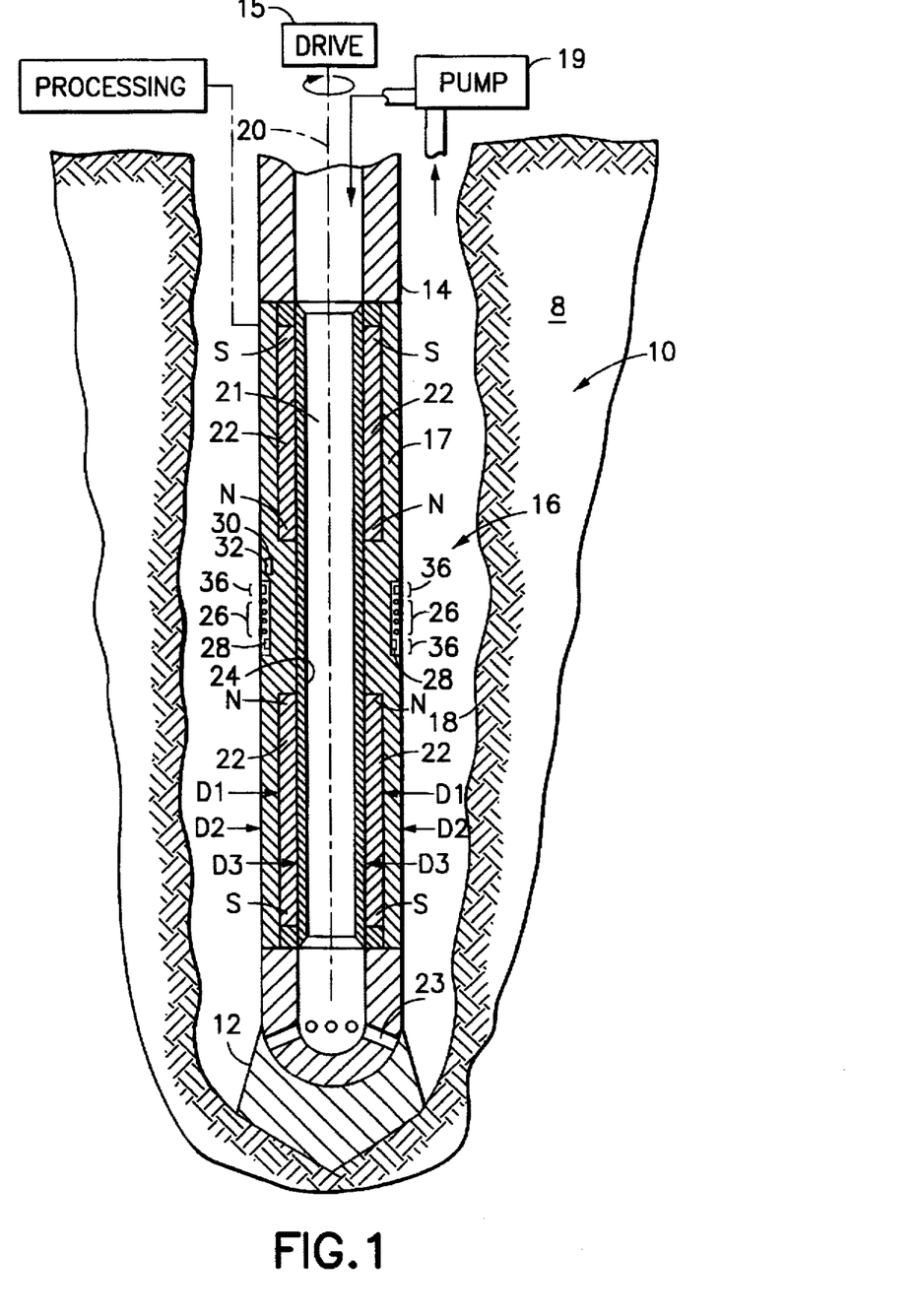
FIG. 1 shows a cross section of a tool for pulsed NMR formation evaluation while drilling.

FIG. 1 shows a tool 10 according to this invention. The tool 10 is generally similar to the assignees' Combined Magnetic Resonance tool (CMR) for Logging While Drilling (LWD) described in U.S. patent application Ser. No. 922,254 to Kleinberg and Sezginer. The tool 10 includes a drill bit 12, drill string 14, and pulsed NMR device 16 (housed within a drill collar 17). The drill bit 12 and drill string 14 comprise a means for drilling a borehole 18 in an earth formation. A drive mechanism 15 rotates the drill string 14 and drill bit 12 as in known in the art. See U.S. Pat. No. 4,949,045 to Clark et al., for example. The drive mechanism can also be a downhole mud-motor placed in the drill string, either above or below the pulsed NMR device 16. If the mud-motor is placed above the NMR device, a drive shaft in channel 21 connects the bit 12 to the mud-motor. The drill collar 17 is made of a nonmagnetic alloy. The tool 10 also comprises a means for making pulsed nuclear magnetic resonance (NMR) measurements while a borehole 18 is being drilled. The pulsed NMR device 16 is connected as part of the drill string 14 and is housed within the drill string 14. As seen in FIG. 1, the pulsed NMR device 16 is rotationally symmetric about a longitudinal axis 20 of the drill string 14.

The borehole 18 typically contains fluid, such as drilling muds. Drilling muds are pumped by pump 19 from the surface through the drill string 14 and drill collar 17 into the borehole 18 and out of the borehole to carry away formation cuttings back to the surface. Such a pump is described in U.S. Pat. No. 4,949,045 to Clark et al., for example. A channel 21 within the drill string 14 comprises a means for carrying the drilling fluid through the drill string 14. The channel 21 is cut within the drill collar 17 substantially parallel to the longitudinal axis 20. The drilling muds exit the channel 21 through ports 23 in the drill bit 12 and enter the borehole 18. Drilling muds inside the drill string 14, drill collar 17 and drill bit 12 are known as "drilling fluids." Drilling muds in the borehole (and fluids which have seeped from the formation) and outside the drill string, collar and bit (14, 17, 12) are known as "borehole fluids." The drill collar 17 and the channel 21 or mud sleeve are made of noncorrodible and nonmagnetic alloys, for example.

The pulsed NMR device 16 comprises, in a preferred embodiment, a pair of tubular magnets 22 arranged and housed in the drill string 14 and within the pulsed NMR device 16 to surround the channel. The two sleeve shaped, tubular magnets 22 are permanently magnetized in the axial direction and are positioned in opposing directions. In FIG. 1 the north magnetic poles of the two tubular magnets 22 face one another, for example. The magnets 22 are preferably made of Samarium-Cobalt-32, which has a high remanence, coercive force, and Curie temperature. The magnets 22 can be installed into a recess that is cut out either from the outside or from the inside of the drill collar 17. Cutting from the inside is preferred because the bending and torsional strengths of the drill collar 17 are proportional to the difference of the fourth powers of the drill collar's outer and inner radii. For example, in FIG. 1 the inner D1 and outer D2 diameters of the drill collar 17 at the magnet-recess are 5.000" and 6.750", respectively. These dimensional values, and those below, are only cited as examples. Numerous other values of the diameters, thickness, and depth are possible.

The magnets 22 are protected from the pressure, cuttings, and abrasion of drilling mud by nonmagnetic steel mud sleeve 24, for example. The sleeve 24 defines the channel 21 and is positioned to isolate the tubular magnets 22 from the drilling mud which circulates to become the borehole fluid. Had the recess for the magnets 22 been made from outside surface of the drilling collar 17, the recess would have to be at most 0.276" deep, for example, in order to achieve the same mechanical strength. This shallow recess must be considered in accommodating the magnets 22 and the protective mud sleeve 24. The external magnetic field of a tubular, axially polarized permanent magnet is proportional to its cross-sectional area, which is a function of the second power of the radius of the magnet. Thus, because the strength of the drill collar is a function of the fourth power of its radii, placing the magnets inside the drill collar yields a smaller collar thickness and a larger magnetic pole strength. It is preferable to cut the recess for the magnets 22 from the inside of the drill collar 17 to obtain greater mechanical strength and sufficient space to accommodate the magnets 22 and steel mud sleeve 24. The magnets as well as the annular region which houses any electronics or any batteries are at atmospheric pressure, for example.

FIG. 1 also shows an RF antenna 26 located in an antenna recess 28 between the two tubular magnets 22. The pulsed NMR portion 16 of this tool 10 comprises the antenna 26 mounted on the drill collar 17 and the two tubular magnets 22. The antenna 26 is mounted in an exterior recess 28 of an exterior surface of the drill collar 17. The antenna recess 28 is preferably on the outside of the drill collar 17, because at the frequency of operation (between 100 kHz and 2 MHz in general) the resulting RF magnetic field could not diffuse out through the drill collar 17.

The antenna 26 preferably comprises a coil which also surrounds the channel. The antenna recess 28 is preferably filled with a nonconducting material such as plastic, fiberglass or rubber. Alternatively, the antenna recess 28 can also be filled with a ferrite to improve the efficiency of the RF antenna 26. The RF antenna 26 can be protected by a sheet-metal shield with axial slots to let out the RF magnetic field. The slotted metallic shield is mounted in the recess 28 and radially outside the antenna 26 coil. Examples of the construction of the antenna and the slotted shield have been described in the U.S. Pat. No. 4,949,045 to Clark et al. issued August 1990 in the context of a Compensated Dual Resistivity Tool (mark of Schlumberger Technology Corporation), and U.S. Pat. No. 4,536,714 to Clark issued August 1985. Alternatively, the shield can be of a non-conductive material, such as ceramic or teflon. Such a shield would attenuate the RF magnetic field less than a sheet-metal shield.

The pulsed NMR portion 16 of this tool 10 also includes driving circuitry. The drill collar 17 includes a compartment 30 in which the driving circuitry 32 is located. The small, atmospheric-pressure compartment 30 close to the RF antenna 26 houses the electronic, driving circuitry such as the Q-switch, duplexer, and preamplifier which drive the antenna and which have to be in close proximity of the RF antenna 26. This driving circuitry 32 is similar to that disclosed in the two U.S. Pat. Nos. to Kleinberg et al., 5,055,787 and 5,055,788.

The NMR device 16 is pulsed and the formation is logged according to the technique described in U.S. Pat. Nos. 5,055,787; 5,055,788; and 5,023,551 to Kleinberg et al. and U.S. patent application Ser. Nos. 800,339 and 999,248 to Sezginer and Sezginer et al, respectively. The information representing the evaluation of the formation is stored in a downhole memory (not shown) and is transmitted up the tool in a manner as described in U.S. Pat. No. 4,949,045 to Clark et al.

Without further precautions, the resonant region of investigation on the formation using a two-magnet design would extend into the borehole and terminate on the tool close to the RF antenna. The borehole signal, according to this invention, is significantly reduced or canceled by shimming magnets. The shimming magnets raise the field strength on the vicinity of the antenna making the borehole nonresonant. The shimming magnets also reduce the gradient of the Larmor frequency in the region of investigation. The shimming magnets comprise portions of a single permanent magnet system. The shimming magnets can be integral with static field producing permanent magnets, or entirely separate from such permanent magnets. Thus, one portion of a permanent magnet system produces a static field in an earth formation under evaluation. Another portion of the permanent magnet system cancels and electromagnetic signal resulting in borehole fluid. Two arrangements of shimming magnets are discussed below.

Figure 2:
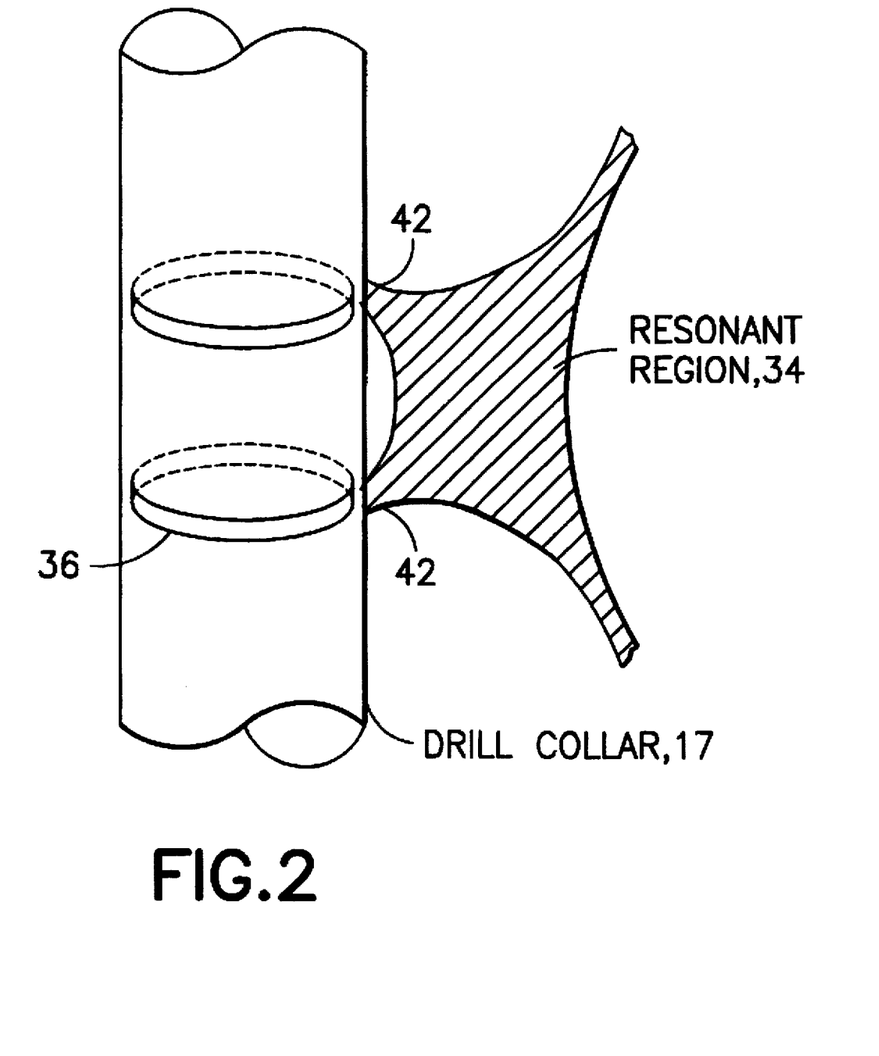
FIGS. 2, 5A, 5B, 6A, and 6B concern fields produced in an earth formation according to the invention.

As discussed in copending U.S. application Ser. No. 922,254, FIG. 2 shows the resonance region 34 extending into the borehole 18. Because the resonance region 34 extends into the borehole 18, an electromagnetic signal, and more specifically a magnetic resonance signal, is produced in the borehole fluid. Such a magnetic resonance signal of the borehole fluid must be eliminated or reduced because the pulsed NMR device 16 functions by detecting protons in fluids. Typically, the rock formation is 0–30% fluid by volume, but the borehole fluid contains more than 50% fluid which has a high density of hydrogen nuclei. For this reason, the magnetic resonance signal of the borehole fluid would dominate any formation signal detected by the pulsed NMR device 16. Magnetic resonance in the borehole fluid can be suppressed by raising the magnitude of the static magnetic field in the borehole so that the Larmor (resonance) frequency in the borehole is above the frequency of the oscillating field produced by the RF coil. Such a field for suppressing magnetic resonance in the borehole fluid can be produced by a permanent magnet 36, which produces magnetic field lines 40. FIG. 2 shows the permanent magnet 36 is wrapped around the longitudinal axis 20 of the drill collar 17, and, thus, around the pulsed NMR device 16. The permanent magnet 36 may be placed in the antenna recess 28, or in a separate recess in the drill collar 17 or on the outer surface of the mud sleeve 24 adjacent the permanent magnets. Most importantly, the permanent magnet 36 is sited to most effectively eliminate the signal from the borehole, such as in the vicinity of the extensions 42 of the resonance region 34. In this manner, the magnetic field lines 40 of the permanent magnet 36 cancel the magnetic resonance signal of the borehole fluid in the vicinity of the extension 42. The location of the extensions 42 of the resonance region 34 is a function of the material, size, shape, and spacing of the static field-producing permanent tubular magnets 22.

According to one embodiment, a shimming magnet is positioned in the groove of the RF antenna. The shimming magnet is radially polarized and is made of a nonconductive material, such as ferrite, so that the shimming magnet does not exclude the field of the RF antenna. One advantage of this embodiment is that the radial thickness of a the resonant region is relatively large, on the order of 28 mm. This large resonant region decreases sensitivity of the NMR measurement to lateral tool motion.

Figure 3A:
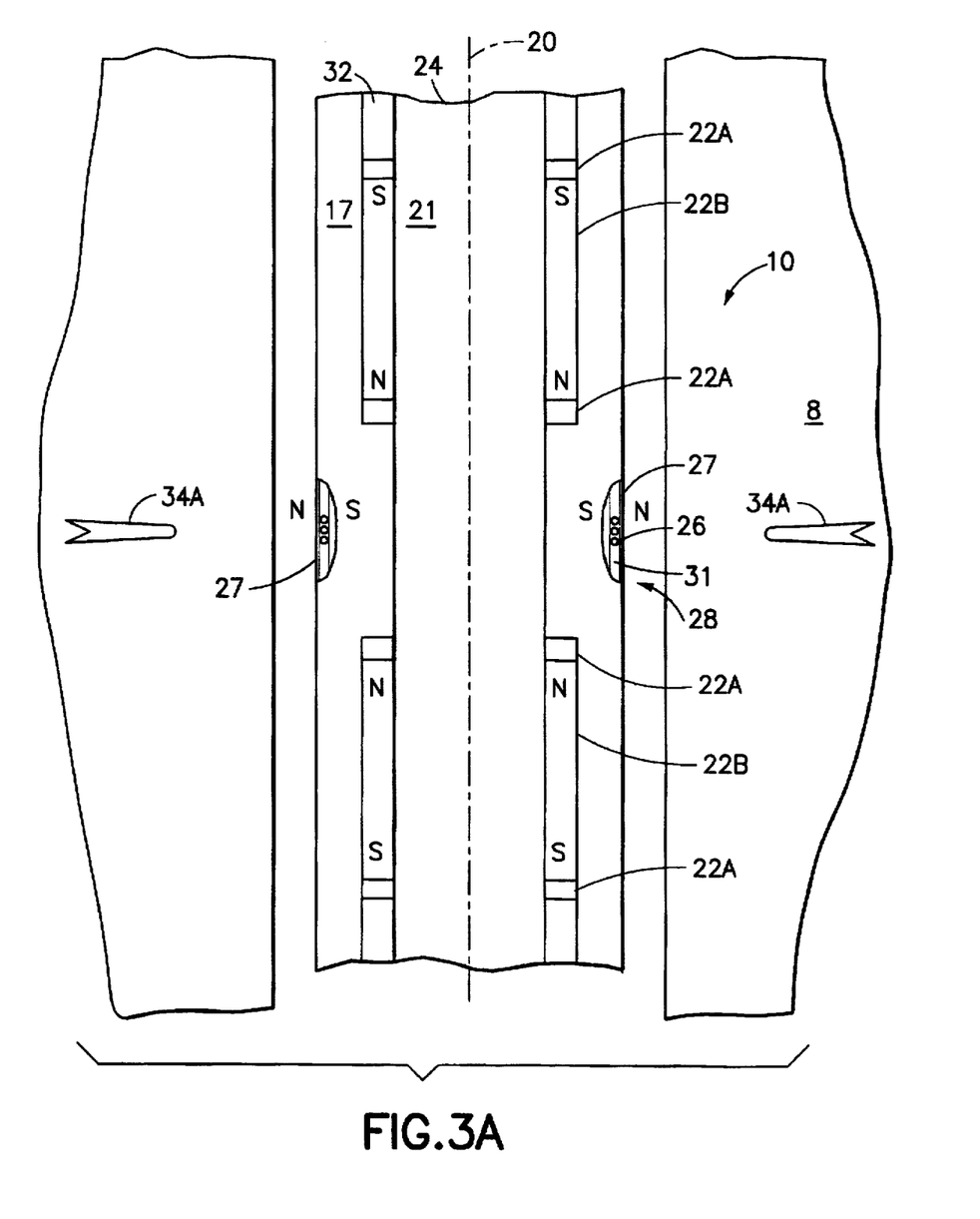
FIGS. 3A, 3B and 4 show shimming magnets.

FIG. 3A shows a cross-section of a portion of the LWD CMR tool 10 along its axis. The figure is rotationally symmetric and its horizontal scale has been expanded for clarity. The parts schematically shown are: the drill collar 17, channel 21, SmCo permanent magnet pole pieces 22A and the Alnico body 22B of a pair of permanent magnets, antenna recess or groove 28, ferrite shimming magnet 31, windings of the RF antenna 26, electronics and battery 32.

The shimming magnet 31 in a recess, whether outside the drill collar or the barrel 24, has a radius which is substantially greater than or substantially less than, respectively, the radius of the permanent magnets 22. In this sense, the shimming magnet 33 is a permanent magnet having a diameter (or other radial dimension) which is substantially different from that of the static field-producing permanent magnets 22. This is a function of the placement of the shimming magnet. It is a mechanical constraint, not a necessity from the point of view of fields.

Figure 3B:
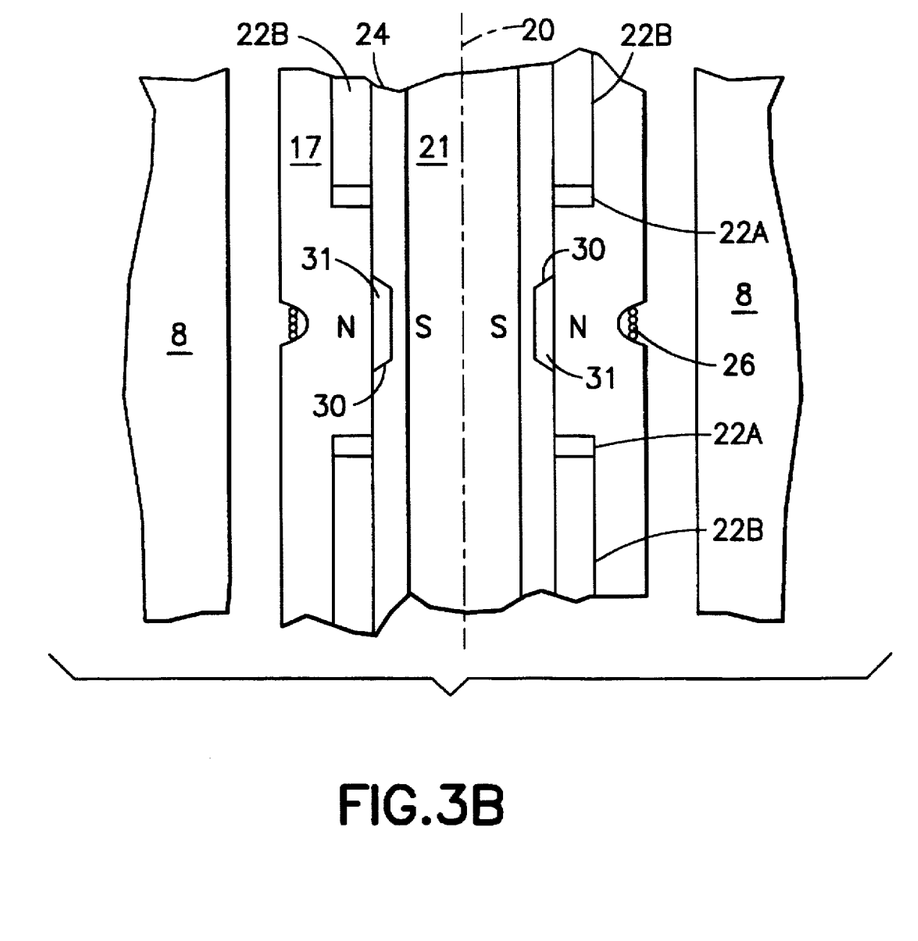

The shimming magnet is radially magnetized. The shimming magnet 31 is sufficiently long in the axial direction to reduce the magnetic resonance borehole signal which is produced by the extensions 42 of the resonant region 34 of FIG. 2. The shimming magnet 31 is positioned in the recess 28 inside the RF antenna 26, for example. Preferably, the shimming magnet 31 is positioned within the drill collar 17 in a recess 30 on the outer surface of the mud sleeve 24, and between the two permanent magnets 22 as shown in FIG. 3B. Such a recess could be on the exterior surface of the barrel 24 so that the drill collar 17 is not weakened and shimming magnet 31 is not exposed to the mud fluid traveling through the channel 21. Such a shimming magnet (FIG. 3B) could have substantially the same axial length but a smaller radius compared to the shimming magnet 31 of FIG. 3A. The shimming magnet 31 would be preferentially made of SmCo, not ferrite.

According to another embodiment, shimming magnets are axially polarized. These shimming magnets are integral extensions of the permanent magnets 22 with their radius stepped down. The north poles of the shimming magnets face each other, for example. Another advantage of this embodiment lies in its construction. The shimming magnets need not be placed in the RF antenna groove and the shimming magnets can be made of the same material (SmCo) as the pole pieces of the main permanent magnets (pole pieces 22A). Use of the same material improves temperature stability.

Figure 4:
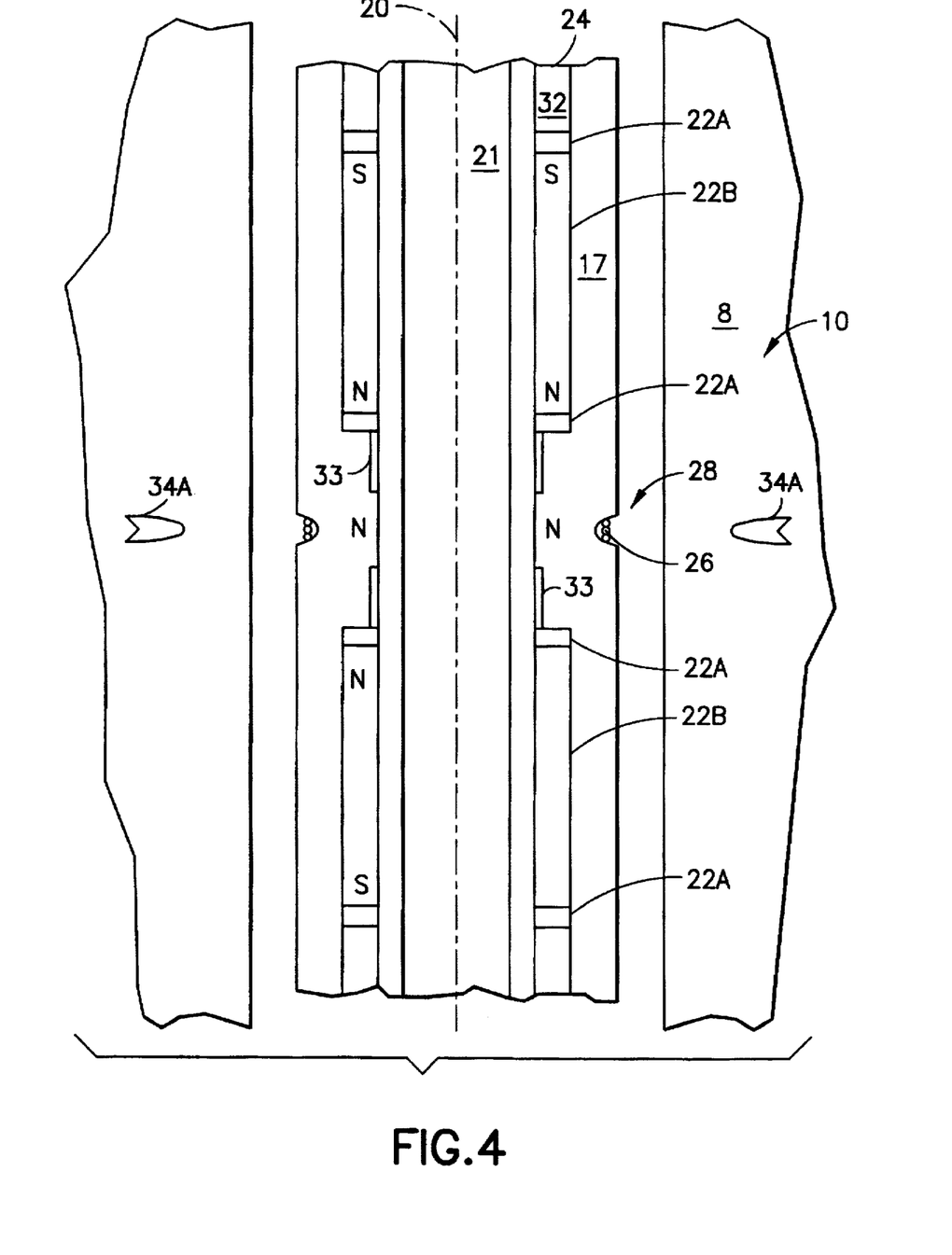

FIG. 4 shows a cross section of a portion of the LWD CMR tool 10 along its axis. The radial scale has been expanded for clarity. Shimming magnets 33 are axially polarized tubular magnets. However, each tubular shimming magnet 33 has a radius which is substantially less than the radius of a permanent magnet 22. Thus, the shimming magnet is a permanent magnet having a radial dimension which is substantially different from that of the static field producing permanent magnets 22. Each shimming magnet 33 is an annular ring encircling the tool 10. (The axial and radial scales are different.)

According to another embodiment, the shimming magnet could have the same radial dimensions as the pair of tubular magnets 22. Such a shimming magnet could be of a material which is magnetically weaker than the tubular magnets 22, and could be placed between the pair of tubular magnets 22.

In fact the size, shape, or material of the shimming magnet is variable. Compensation for a particular choice of size, shape, or material can be made by adjusting the other two. It is important that the shimming magnet, of whatever size, shape or material, is designed to produce a field which cancels or reduces the magnetic resonance signal of the borehole fluid, and makes the static field sufficiently uniform in the region of investigation.

FIGS. 3A and 4 show that the pulsed NMR device 16 produces a resonance region 34A that is rotationally symmetric about the axis 20. The resonance region 34A is in the formation 8 under evaluation. In all cases, including that of FIG. 3B, the shimming magnets of this invention have reduced or canceled the borehole signal by eliminating extensions of the resonant region.

Figure 5A:
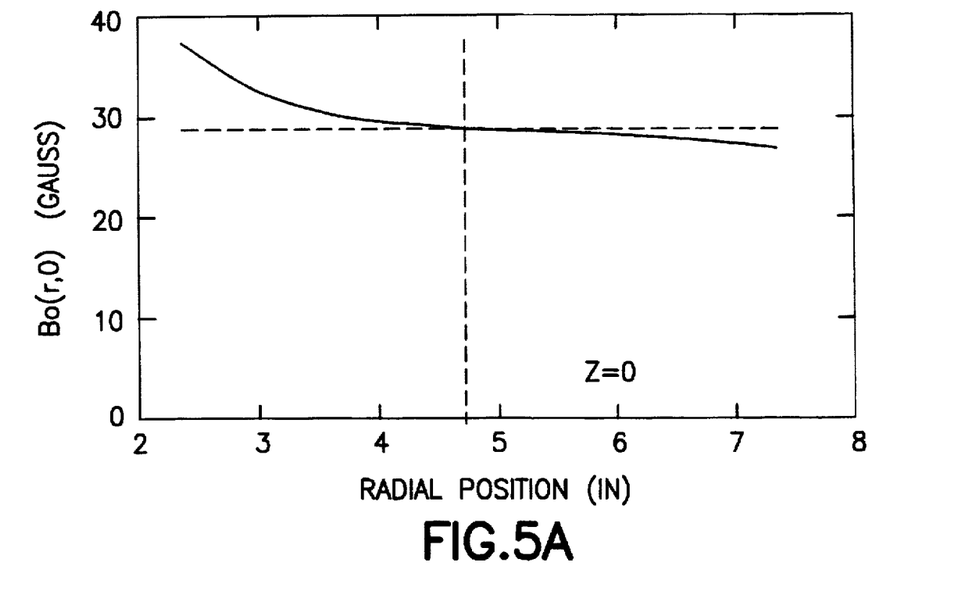
Figure 5B:
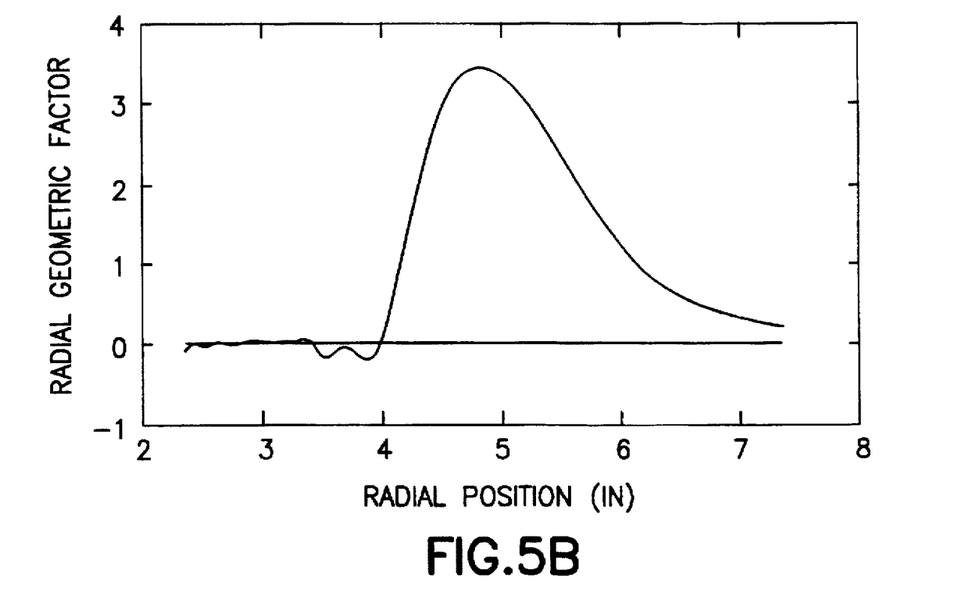

FIGS. 5A, 5B concern the embodiment of FIG. 3A. These figures indicate that the shimming magnet 31 has increased the magnetic field near the borehole and canceled the electromagnetic signal of the borehole fluid. FIG. 5A indicates that the variation of the static field as a function of radius in the symmetry plane (z=0) transverse to the axis. FIG. 5B indicates the radial sensitivity (geometric factor) as a function of radial position. FIG. 5B results by integrating the resonant region of FIG. 3A.

Figure 6A:
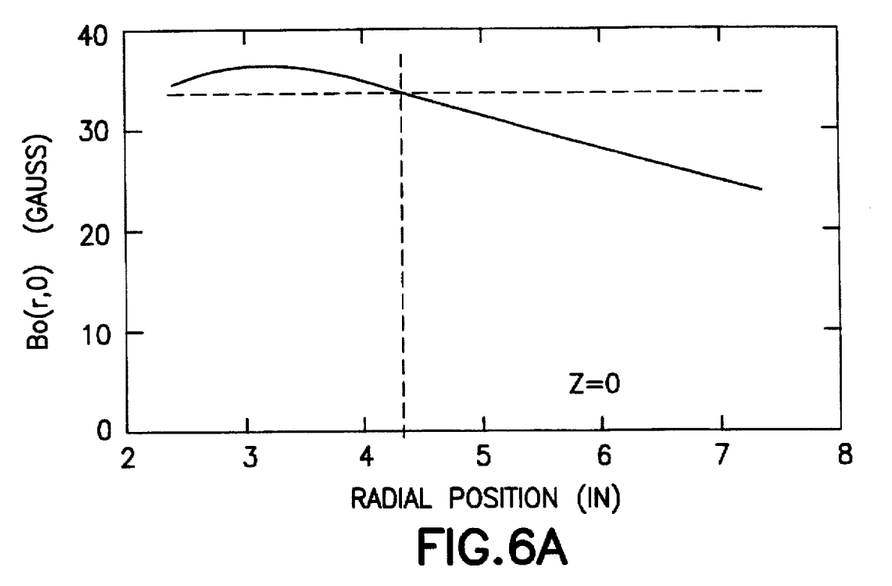
Figure 6B:
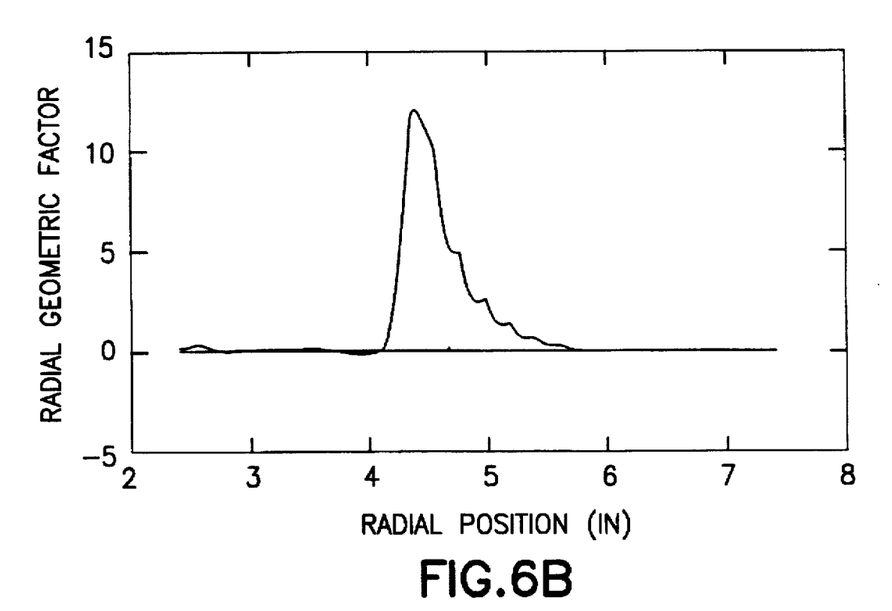

FIGS. 6A and 6B concern the embodiment of FIG. 4. These figures indicate that the shimming magnets 33 have increased the magnetic field near the borehole and canceled the electromagnetic signal of the borehole fluid. FIG. 6A illustrates that variation of the static field as a function of radius in the symmetry plane (z=0) transverse to the axis. FIG. 6B illustrates radial sensitivity (geometric factor) as a function of radius. FIG. 6B results by integrating the resonant region of FIG. 4.

The CDR antenna described in U.S. Pat. No. 4,949,045 for use in this application could be modified. Specifically, the antenna groove can be covered by a 10-mil thick copper sheet. Copper Litz wire can be used as the winding to the antenna. The windings can be placed farther out in the radial direction, immediately below the shield.

Figure 7:
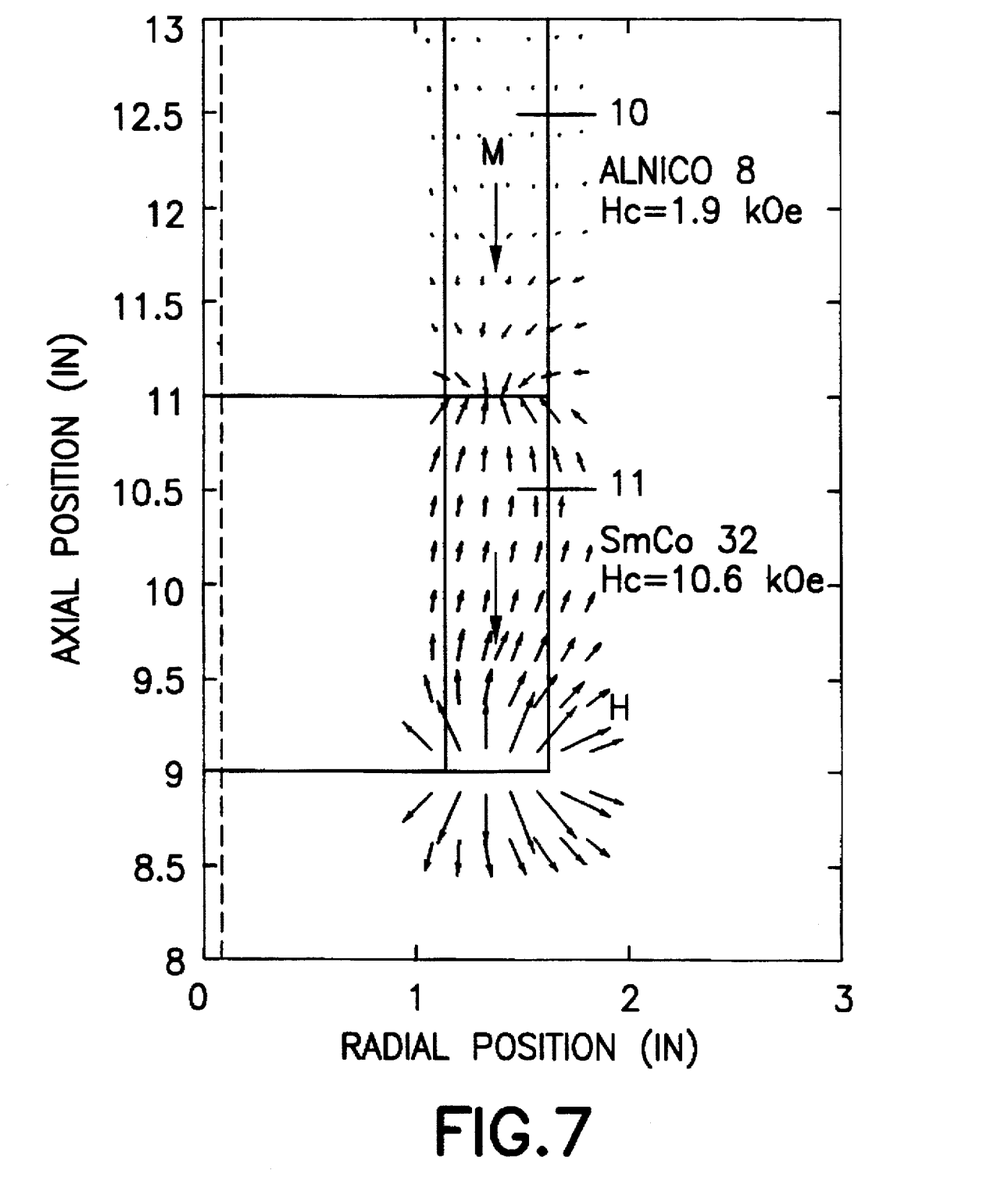
FIG. 7 shows a dual material permanent magnet.

FIG. 7 illustrates a dual-material permanent magnet 22. One material of lower coercive force and lower cost (Alnico) is used in the mid-portion of the magnet 22B where the demagnetizing field ($\overline{H}$) is small. SmCo-32 is used in the end portions of the magnet 22A. This measure cuts the cost of the magnet 22 by a factor of 3 to 4.

Figure 8:
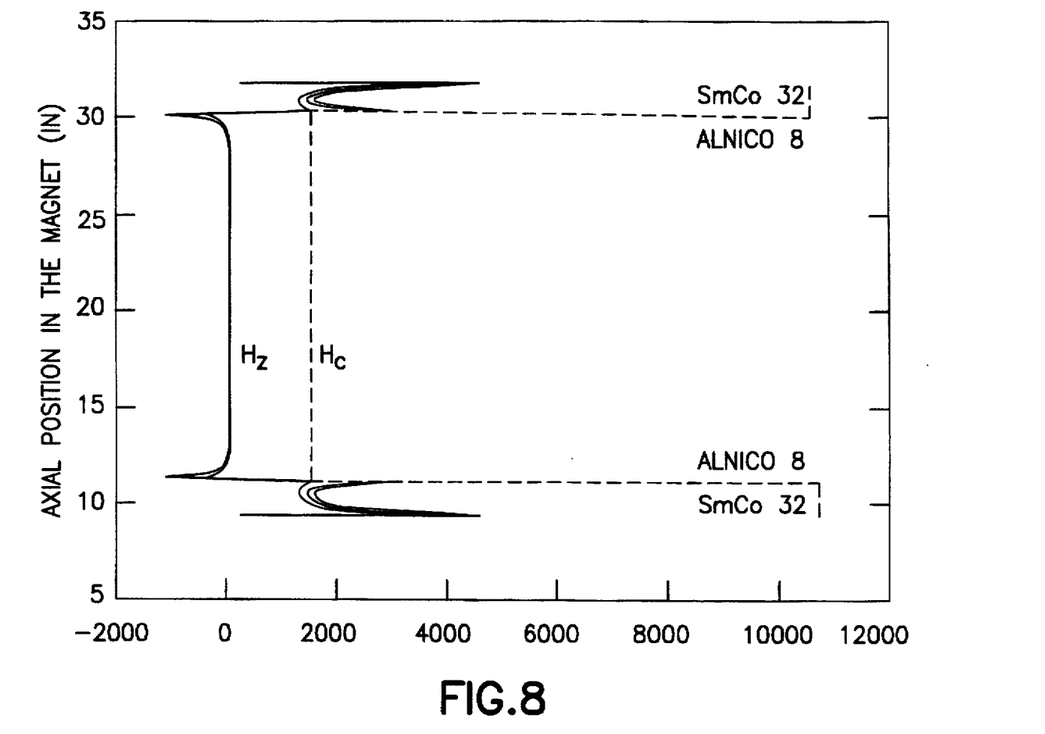
FIG. 8 illustrates demagnetizing force of the magnet of FIG. 9.

FIG. 8 uses solid curves to illustrate that the demagnetizing force $H_z$) in the main magnet as a function of axial position z at several radial positions from the inner radius (1.125 in.) to the outer radius (1.625 in.) of the tubular magnet. The dashed line indicates that the coercive force of the composite magnet is larger than the demagnetizing force at all points. Alnico 8 has an $H_c$ of 1.9 kOe while SmCo-32 has an $H_c$ of 10.6 kOe. Thus, the use of dual-material magnets would not substantially affect operation of the tool 10.

A typical drilling penetration rate in sedimentary formations, that is 60 ft/hr., is a factor of 10 slower that the logging speed of an NMR wireline wool, (e.g., CMR). Through the same vertical travel, the LWD CMR would acquire 10 times as many CPMG's, compared to the wireline tool. Therefore, it is sufficient to collect 10 times fewer echoes per CPMG thus increasing the tool's immunity to lateral and axial vibrations. In addition, the pulse sequence can be modified as discussed below.

Vibration Tolerant Pulse Sequence

During a Carr-Purcell-Meiboom-Gill (CPMG) sequence, as described in U.S. Pat. No. 5,363,041, to Sezginer and Ser. No. 800,339 to Sezginer, et al. (the disclosures of which are incorporated by reference), while a sequence of spin-echoes are being recorded, the measurement is sensitive to displacements of the logging while drilling tool. This window of vulnerability is 10–500 msec long, depending on the number of spin-echoes per CPMG sequence. A 10 mm radial or axial displacement during a CPMG sequence will cause an erroneous reduction in the signal. The measurement is made tolerant to vibrations by keeping CPMG sequences short. A measurement sequence such as $$T_L \text{ CPMG}^{(+)} \, T_L \text{ CPMG}^{(-)} \, T_s \text{ CPMG}^{(+)} \, T_s \text{ CPMG}^{(-)} \ldots$$

where $T_L$ is a long recovery time (1 second or longer) and $T_s$ is a short recovery time (typically 20 msec) and each CPMG sequence yields a short train of spin-echoes: CPMG$^{(\pm)}=90°_{\pm x}[t_{cp} \, 180°y.t_{cp}\pm\text{echoj}]$ repeat for j=1,2, ... J and $t_{cp}$ is half of the echo spacing (about 0.2 ms). $90°_{\pm x}$ denotes an RF-pulse that causes the spins to rotate by a 90° angle about the axis $\pm x$. Similarly $180_y$ denotes an RF-pulse that causes a rotation by 180° about the axis y. The z-axis is parallel to the static field, the x-axis is in the direction of the circularly polarized component of the RF-field ($B_1$) that rotates in the same direction as the spins precess. The reference frame (x,y,z) rotates around the z axis with the angular frequency of the RF-field.

The spin echoes of the CPMG$^{(-)}$ sequence are subtracted from the spin echoes of the preceeding CPMG$^{(+)}$ sequence. This operation cancels any spurious baseline in the measurement. The key to making the measurement tolerant to vibrations is to make the length of each CPMG sequence (2 $t_{cp}$J) so short, for example 10 ms, that the drill collar cannot be displaced by a significant fraction of the vertical or radial extent of the sensitive region during a CPMG sequence. The CPMG sequences following the long recovery time $T_L$ give an indication of the bound fluid volume. The difference of porosity and BFV give the unbound fluid volume (free fluid index).

We claim:

1. A method for determinng a characterisitc of formations surrounding a borehole, comprising:

drilling the borehole in the earth formation;

using a tool to drill the borehole;

directing fluid through the tool and into the borehole;

using the tool to obtain NMR measurements while the borehole is being drilled;

generating, from the tool, a sufficiently short sequence of magnetic pulses to minimize $2t_{cp}J$ such that the NMR measurements are tolerant to vibrations of the tool while the borehole is being drilled, where $t_{cp}$ is the Carr-Purcell spacing and J is the number of echoes collected in a single Carr-Purcell-Meiboom-Gill (CPMG) sequence; and determining a characterisitc of the formation.

2. The method of claim 1 wherein $2t_{cp}J$ is approximately ten milliseconds.

3. The method of claim 2 wherein the formation characterisitc is the bound fluid volume.

4. The method of claim 2 wherein the formation characterisitc is the porosity.

5. The method of claim 2 wherein the formation characterisitc is the unbound fluid volume.

6. The method of claim 1 wherein the truncated pulse sequence is less than ten milliseconds.

7. The method of claim 6 wherein the formation characterisitc is the bound fluid volume.

8. The method of claim 6 wherein the formation characterisitc is the porosity.

9. The method of claim 6 wherein the formation characterisitc is the bound fluid volume.

* * * * *